(12) United States Patent
Bjernulf

(10) Patent No.: US 10,343,083 B2
(45) Date of Patent: Jul. 9, 2019

(54) SYSTEM AND METHOD FOR CONTROLLING A LIQUID CHROMATOGRAPHY SYSTEMS

(71) Applicant: GE Healthcare Bio-Sciences AB, Uppsala (SE)

(72) Inventor: Olle Bjernulf, Uppsala (SE)

(73) Assignee: GE Healthcare Bio-Sciences AB, Uppsala (SE)

(*) Notice: Subject to any disclaimer, the term of this patent is extended or adjusted under 35 U.S.C. 154(b) by 35 days.

(21) Appl. No.: 14/422,793

(22) PCT Filed: Aug. 22, 2013

(86) PCT No.: PCT/SE2013/050988
§ 371 (c)(1),
(2) Date: Feb. 20, 2015

(87) PCT Pub. No.: WO2014/031070
PCT Pub. Date: Feb. 27, 2014

(65) Prior Publication Data
US 2015/0246297 A1 Sep. 3, 2015

(30) Foreign Application Priority Data
Aug. 24, 2012 (SE) .................................. 1250951

(51) Int. Cl.
*B01D 15/16* (2006.01)
*G01N 30/86* (2006.01)
(Continued)

(52) U.S. Cl.
CPC .......... *B01D 15/163* (2013.01); *G01N 30/24* (2013.01); *G01N 30/32* (2013.01); *G01N 30/36* (2013.01);
(Continued)

(58) Field of Classification Search
CPC ...... B01D 15/163; B01D 15/16; G01N 30/24; G01N 30/8658; G01N 30/32; G01N 30/36
See application file for complete search history.

(56) References Cited

U.S. PATENT DOCUMENTS 4,767,279 A 8/1988 Dourdeville
5,467,635 A 11/1995 Nakagawa et al.
(Continued)

FOREIGN PATENT DOCUMENTS

CN 101400418 A 4/2009
EP 0327609 B1 9/1996
(Continued)

OTHER PUBLICATIONS

Corresponding Chinese Application No. 201380043971.8 issued Office Action dated Jan. 20, 2016.
(Continued)

*Primary Examiner* — Krishnan S Menon
*Assistant Examiner* — Waqaas Ali
(74) *Attorney, Agent, or Firm* — Wood IP LLC

(57) ABSTRACT

Method for controlling a liquid chromatography system comprising a system pump and a column in fluid communication with the system pump by a fluid flow path, the method comprising the steps: registering the system pressure at a flow path position close to the system pump, controlling the operation of the system pump in response to the registered system pressure, estimating a pre-column pressure based on the registered system pressure, the characteristics of the flow path, and the viscosity and flow-rate of the liquid in the system, and controlling the operation of the system pump in response to the estimated pre-column pressure.

10 Claims, 4 Drawing Sheets

(51) Int. Cl.
*G01N 30/24* (2006.01)
*G01N 30/32* (2006.01)
*G01N 30/36* (2006.01)

(52) U.S. Cl.
CPC ......... *G01N 30/8658* (2013.01); *B01D 15/16* (2013.01)

(56) References Cited

U.S. PATENT DOCUMENTS

| | | |
|---|---|---|
| 6,641,783 B1 | 11/2003 | Pidgeon et al. |
| 7,670,480 B2 | 3/2010 | Witt et al. |
| 7,811,758 B2 | 10/2010 | Mori et al. |
| 8,205,485 B2 | 6/2012 | Suzuki et al. |
| 9,103,814 B2 | 8/2015 | Ciavarini et al. |
| 9,618,485 B2 | 4/2017 | Witt |
| 2003/0116195 A1 | 6/2003 | Weissgerber et al. |
| 2004/0020308 A1 | 2/2004 | Jochum |
| 2006/0219618 A1* | 10/2006 | Witt ............... G01N 30/32 210/198.2 |
| 2008/0275228 A1 | 11/2008 | Mori et al. |
| 2009/0205409 A1* | 8/2009 | Ciavarini ............ G01N 30/34 73/61.56 |
| 2013/0248451 A1 | 9/2013 | Hall et al. |

FOREIGN PATENT DOCUMENTS

| | | | |
|---|---|---|---|
| EP | 1543321 A2 | 6/2005 | |
| EP | 1324033 B1 | 9/2006 | |
| EP | 1996303 A2 | 12/2008 | |
| EP | 2124047 A1 | 11/2009 | |
| EP | 2210086 A1 | 7/2010 | |
| EP | 1707958 B1 | 1/2011 | |
| EP | 1730273 B1 | 8/2013 | |
| EP | 2675540 A1 | 12/2013 | |
| EP | 2888584 A1 | 7/2015 | |
| JP | 59-157563 A | 9/1984 | |
| JP | 10-2770 A | 1/1998 | |
| JP | 2005-278438 A | 10/2005 | |
| JP | 2006-284556 A | 10/2006 | |
| JP | 2009-530615 A | 8/2009 | |
| JP | 2009-281897 A | 12/2009 | |
| JP | 5802760 B2 | 11/2015 | |
| WO | 1988/010460 A2 | 12/1988 | |
| WO | WO0045929 A * | 8/2000 | |
| WO | WO 0045929 A1 * | 8/2000 | ............ G01N 30/20 |
| WO | 2004/013578 A2 | 2/2004 | |
| WO | 2005/093053 A1 | 10/2005 | |
| WO | 2006/103133 A1 | 10/2006 | |
| WO | 2007/109157 A2 | 9/2007 | |
| WO | 2009/062538 A1 | 5/2009 | |
| WO | 2012/074481 A1 | 6/2012 | |
| WO | 2014/031070 A1 | 2/2014 | |

OTHER PUBLICATIONS

General Physics, Qing-Guo Zhang et al., China Agriculture Press, p. 40, "Poiseuille's law", Jan. 31, 2012.
English translation of Second Office Action for Chinese Patent Appl. No. 201380043971.8, filed Sep. 27, 2016, 18 pages.
English translation of Supplementary Chinese Search report from Chinese Patent Application No. 201380043971.8, filed Aug. 22, 2013, 2 pages.
Office Action Received for Japanese Patent Application No. 2015-528440, dated Jul. 18, 2017, 5 Pages (2 Page English Translation of Reference Details + 3 Pages Official Copy).
International Search report and Written Opinion Received for PCT Patent Application No. PCT/SE2013/050988, dated Nov. 25, 2013, 10 pages.
International Preliminary Report on Patentability Received for PCT/SE2013/050988, dated Mar. 5, 2015, 8 Pages.
Supplementary European Search Report Received for European patent Application No. 13830476.1, dated Jun. 8, 2016, 8 Pages.

* cited by examiner

SYSTEM AND METHOD FOR CONTROLLING A LIQUID CHROMATOGRAPHY SYSTEMS

FIELD OF THE INVENTION

The present invention relates to a system and method for controlling a liquid chromatography system and in particular for controlling the column pressure.

BACKGROUND

In many liquid chromatography systems the pressure over the column is monitored in order to protect the column hardware and the column media from too high pressures.

SUMMARY OF THE INVENTION

The object of the invention is to provide a system and method for controlling a liquid chromatography system, which valve overcomes one or more drawbacks of the prior art. This is achieved by the system and method as defined in the independent claims.

One advantage with the present invention is that a chromatography system may be controlled to run safely at pressures closer to the column pressure limit without the need for an additional pressure sensor at the column.

According to one aspect, there is provided a method for controlling a liquid chromatography system comprising a system pump and a column in fluid communication with the system pump by a fluid flow path, the method comprising the steps:

registering the system pressure at a flow path position close to the system pump, controlling the operation of the system pump in response to the registered system pressure, estimating a pre-column pressure based on the registered system pressure, the characteristics of the flow path, and the viscosity and flow-rate of the liquid in the system, and controlling the operation of the system pump in response to the estimated pre-column pressure.

In one embodiment the pre-column pressure is estimated based on Bernoulli's formula:

Flow channel $\Delta P$ [MPa]=$0.000000000679*L*Q*V/D^4$ wherein
L=length of the fluid flow path [mm]
D=diameter of the fluid flow path [mm]
Q=flow rate [ml/min]
V=viscosity [cP]

In one embodiment the step of controlling the operation of the system pump in response to the estimated pre-column pressure involves restricting the pre-column pressure below a predefined value.

In one embodiment the predefined value is a pressure limit for the column.

In one embodiment the pressure limit for the column is accessed from a columns property table stored in a system controller associated with the chromatography system.

According to another aspect, there is provided a liquid chromatography system comprising a system pump and a column in fluid communication with the system pump by a fluid flow path, and a system controller arranged to:

register, by a system pressure sensor, the system pressure at a flow path position close to the system pump, control the operation of the system pump in response to the registered system pressure, estimate a pre-column pressure based on the registered system pressure, the characteristics of the flow path, and the viscosity and flow-rate of the liquid in the system, and control the operation of the system pump in response to the estimated pre-column pressure.

A more complete understanding of the present invention, as well as further features and advantages thereof, will be obtained by reference to the following detailed description and drawings.

DETAILED DESCRIPTION OF EMBODIMENTS OF THE INVENTION

Figure 1:
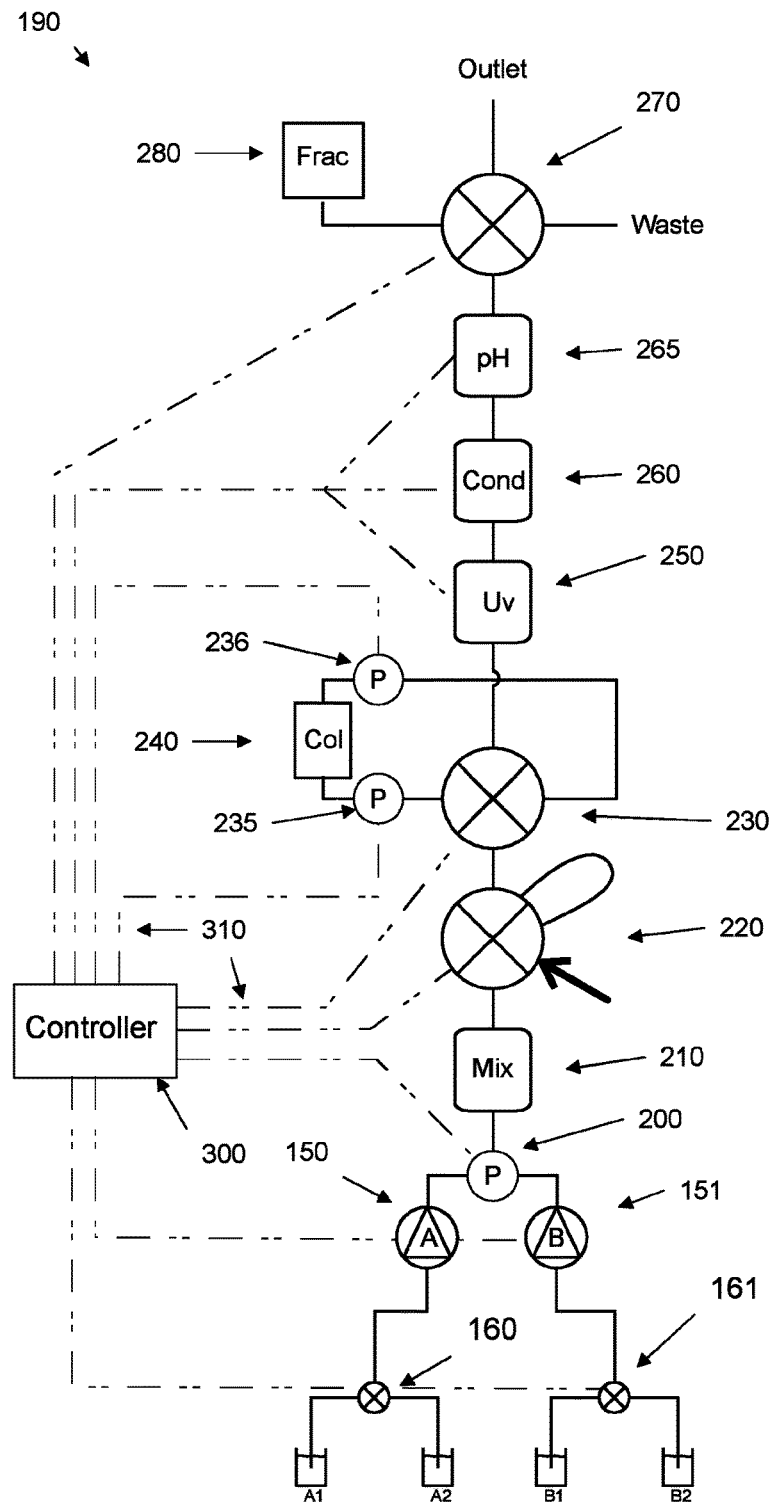
FIG. 1 is a schematic flow chart of an example of a liquid chromatography system.

In a liquid chromatography system (LC-system) back pressure will be generated when running liquid through the system. If the back pressure exceeds any of the set pressure limits, an alarm will be triggered and the system will stop. This may be one of the most common problems in chromatography.

Definitions

| Pressure | Description |
|---|---|
| System pressure | The highest pressure in the system, normally measured directly after the system pump. |
| Pre-column pressure | The pressure before the column. |
| Post-column pressure | The pressure after the column. |
| Delta-column pressure | The differential pressure over the column defined as the difference between pre-column and post-column pressure. |
| Pressure limit | The specification for the maximum allowed pressure. Limits can exist for system pressure, pre-column pressure and delta-column pressure. |
| Pressure alarm | The function in the system that stops the run if the pressure exceeds a pressure limit Alarms can exist for system pressure, pre-column pressure and delta-column pressure. |

The pre-column pressure affects the column hardware. The pressure affecting the column hardware depends on the back pressure generated by the column itself and the back pressure generated by the system after the column. If the pressure limit for the column hardware is exceeded, the column might start leaking.

Delta-column pressure may also be referred to as pressure drop or ΔP. This pressure affects the chromatography medium within the column. The pressure affecting the packed bed depends only on the flow rate and viscosity of the solution and not on the system. When the flow rate is too high and/or a high-viscosity solution is used, the pressure limit for the packed bed might be exceeded. The packed bed pressure limit is the maximum allowed pressure drop over the packed bed. When the pressure limit is exceeded, the particles of the chromatography medium become distorted and/or are forced to the bottom of the column and cause the back pressure to increase. This leads to gap formation or a collapse of the packed bed, resulting in poor chromatographic performance.

System pressure is generated by the complete system flow path and most systems measure this pressure at the system pump. Some systems have additional pressure sensors before and after the column that allow calculation of the pressure drop (Δp) over the column.

Many systems have only one pressure sensor placed directly after the pump to register the system pressure. To protect the column hardware the only available pressure sensor is then used to control the system pressure to not exceed the pressure limit for the weakest component in the flow path, which often is the column, even if it does not measure the pre-column pressure. The measured system pressure will always be higher than the actual pre-column pressure. This will lead to either a situation where the column cannot be run in the full operating range or a situation where the pressure alarm is set to a higher value than the pressure limit for the column in order to compensate for the pressure difference between the pressure sensor and the column. The latter is rather dangerous since this pressure difference is dependent on variable factors such as flow rate, viscosity and the components in the flow path.

Some systems, e.g. ÄKTA avant, have multiple pressure sensors. In these systems the pre-column and delta-column pressure limits can be used directly to set the corresponding pressure alarms. The disadvantage with this system design is of course the higher production cost with multiple pressure sensors.

FIG. 1 schematically shows one embodiment of a chromatography system 190 comprising two 3-way input-valves 160 and 161, arranged to select the input fluid from fluid sources A1, A2, B1, B2 for two system pumps 150 and 151. Said chromatography system 190 may further comprise:
- a pressure sensor 200 for registering the system pressure in the flow path after the system pumps,
- a mixer 210 to ensure appropriate mixing of the fluids supplied by the pumps,
- an injection valve 220 for injecting a sample into the fluid path,
- a column connection valve 230 for selectively connecting/disconnecting a column 240 in the fluid path.
- a pre-column pressure sensor 235 and a post-column pressure sensor 236
- an ultraviolet (UV) monitor 250 for detecting the output from the column.
- a conductivity monitor 260,
- a pH monitor 265,
- an output selection valve 270 with two or more output positions, e.g. connected to a fraction collector 280, a waste receptacle or the like and
- a system controller 300 connected to pumps and valves for controlling the liquid flow through the system, and to sensors and monitors for monitoring the flow, connections being illustrated by dotted lines 310.

The chromatography system of FIG. 1 represents a general example of how a chromatography system may be designed, and other embodiments may be of different design comprising two or more of some components and potentially lack some of said components. According to one embodiment, the chromatography system is a liquid chromatography system.

Figure 2:
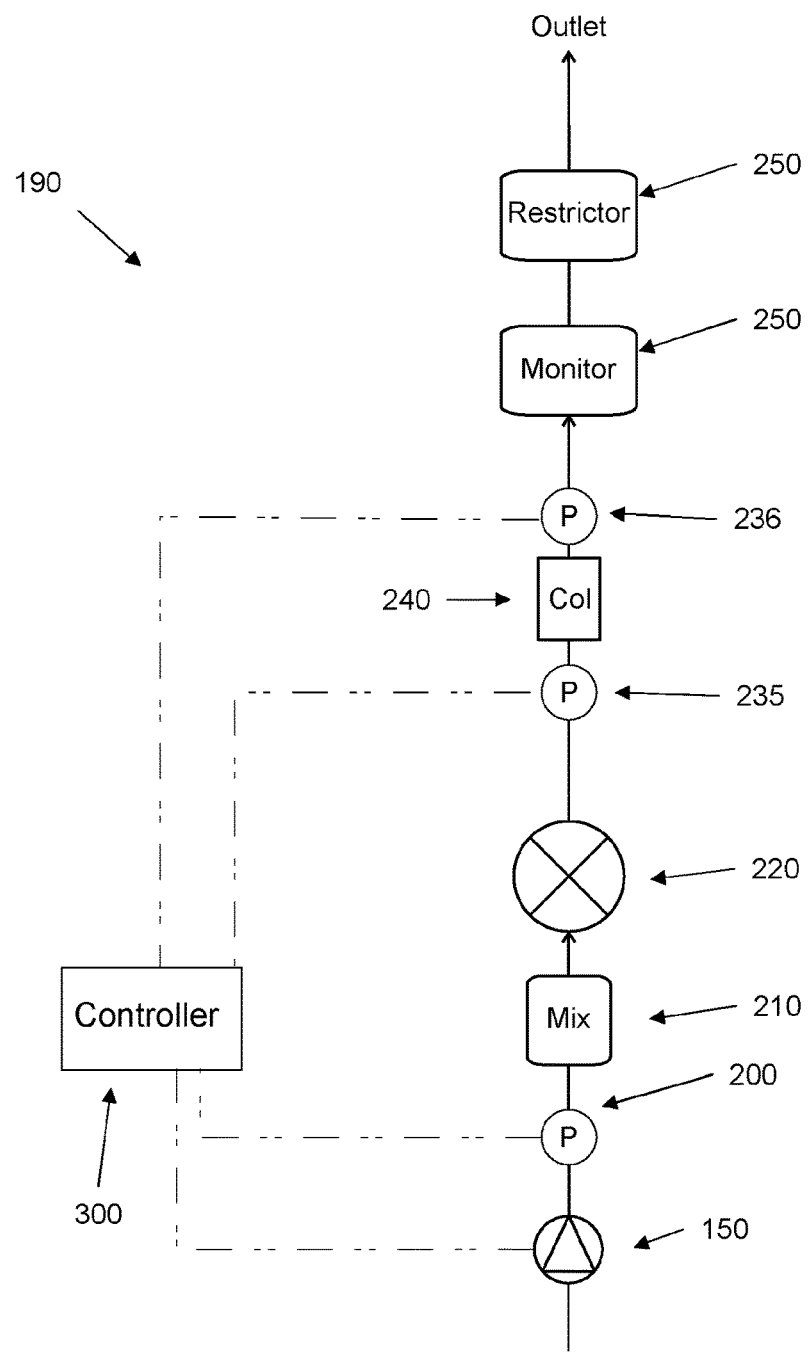
FIG. 2 is a simplified flow chart for a liquid chromatography system according to FIG. 1.

FIG. 2 is a simplified flow chart for a liquid chromatography system 190 according to FIG. 1. In FIG. 2 the flow path has been straighten out and some components have been removed to achieve a more simplistic view. In FIG. 2 the system controller is shown connected only to the pump 150, the pressure sensor 200, the pre-column pressure sensor 235 and the post-column pressure sensor 236, but it may be connected to other components as discussed above. In FIG. 2, the system comprises both the pre-column pressure sensor 235 and the post-column pressure sensor 236, whereby the column pressure is directly measured by the pre-column sensor 235, and the delta-column pressure by subtracting the pressure registered by the post-column sensor 236 from the column-prerssure.

Figure 3:
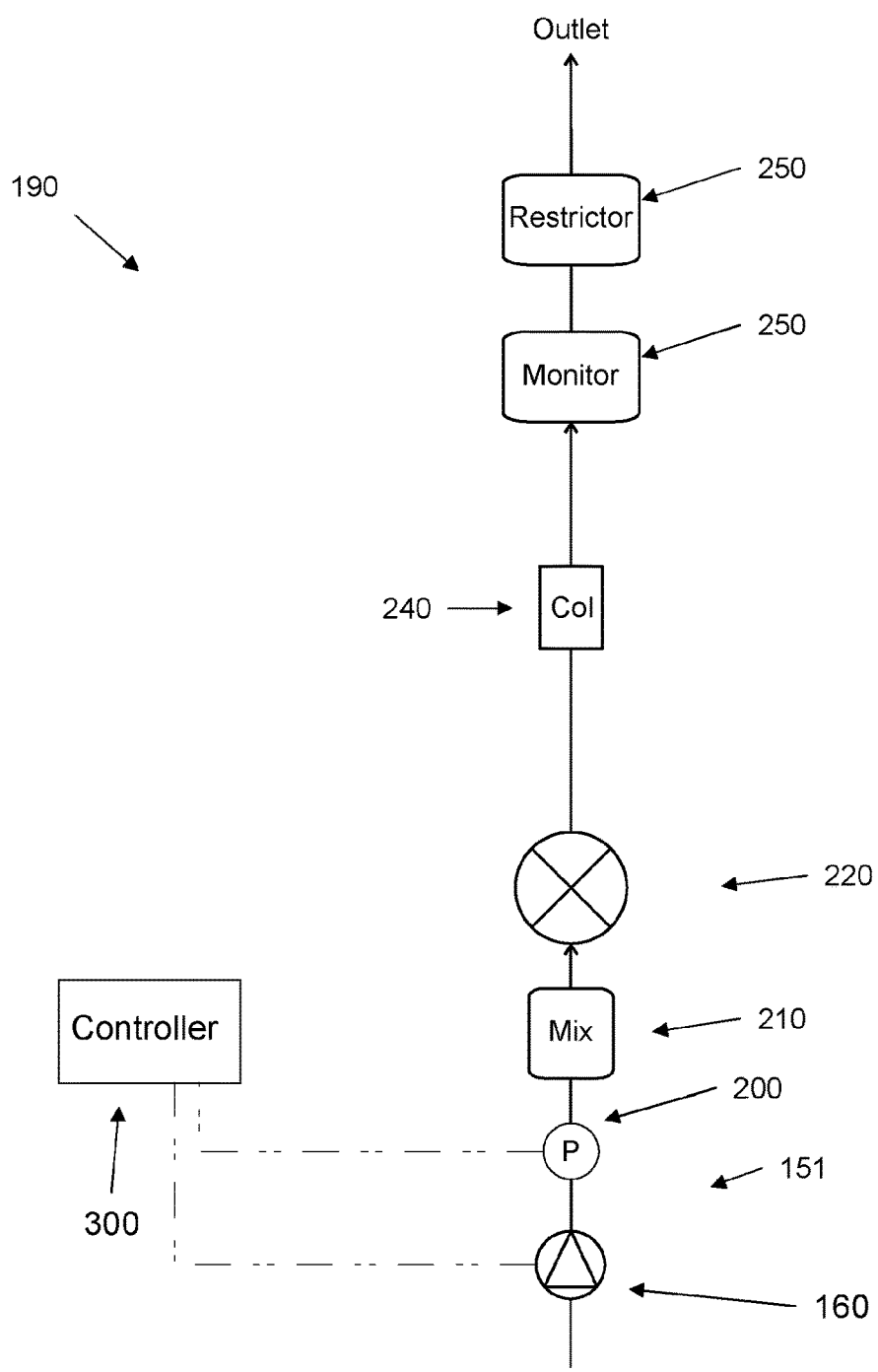
FIG. 3 is a simplified flow chart of a liquid chromatography system with one single pressure sensor for registering the system pressure.

As briefly mentioned above, some systems do not have other pressure sensors, than the system pressure sensor 200. FIG. 3 is a simplified flow chart of such a liquid chromatography system 190 with one single pressure sensor 200 for registering the system pressure. As mentioned above, the pressure control in such a system only relies on the registered system pressure, by sensor 200.

Figure 4:
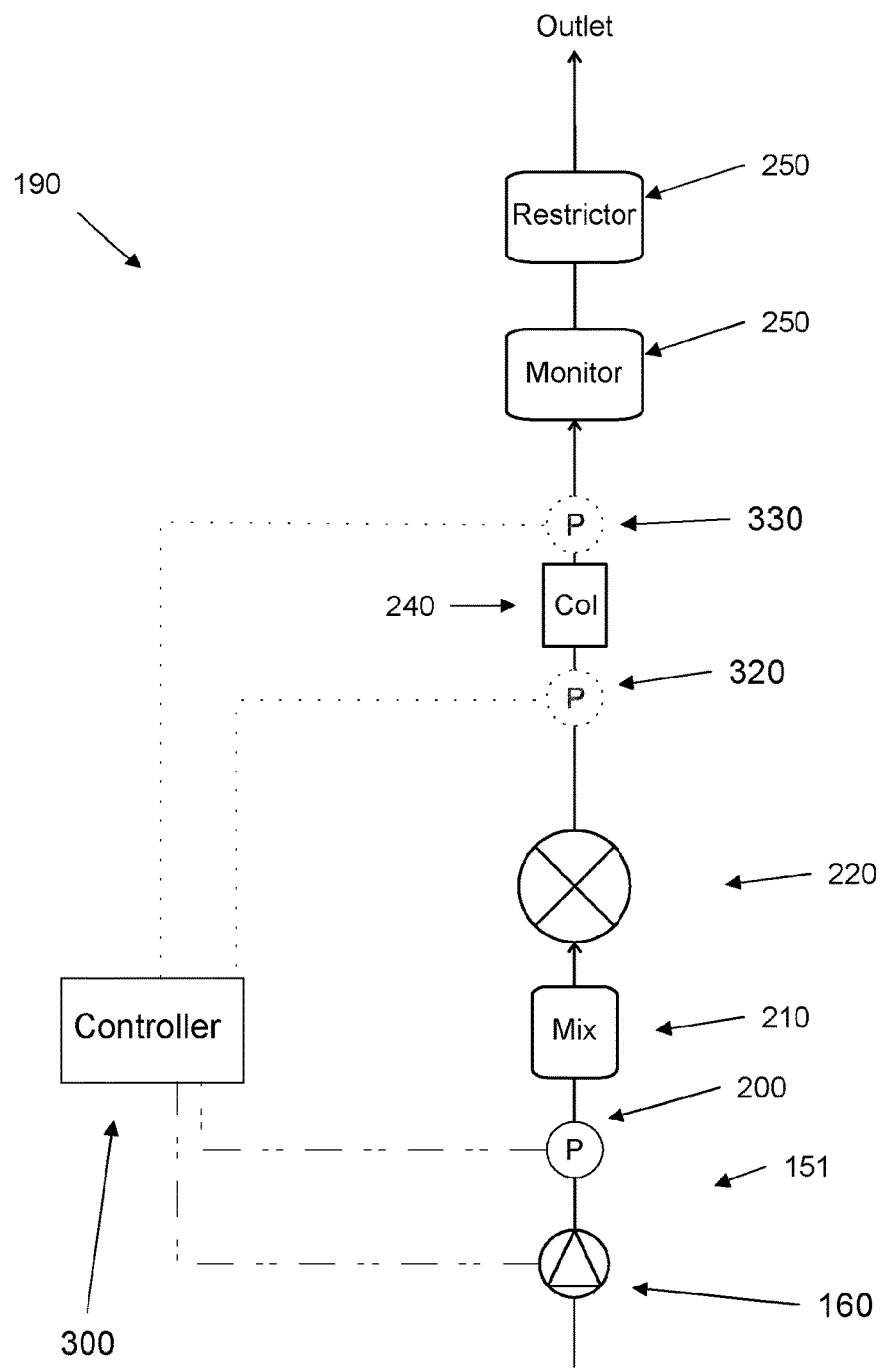
FIG. 4 is a simplified flow chart of a liquid chromatography system according to one embodiment of the present invention.

FIG. 4 is a simplified flow chart of a liquid chromatography system according to one embodiment of the present invention, wherein the controller 300 is arranged to estimate the pre-column pressure based on the registered system pressure, the characteristics of the flow path, and the viscosity and flow-rate of the liquid in the system. The estimated pre-column pressure may be referred to as a "virtual pressure sensor" schematically shown in FIG. 4 by faint dotted lines.

According to one embodiment, the calculation of the virtual pressure signal may be based on Bernoulli's formula for pressure drop in a flow channel.

$$\text{Flow channel } \Delta P \text{ [MPa]} = 0.000000000679 * L * Q * V / D^4$$

where
L=length [mm]
D=diameter [mm]
Q=flow rate [ml/min]
V=viscosity [cP]

By providing length and diameter of the flow path, and the viscosity of the liquid in the system, to the system controller, it may be arranged to calculate the pressure drop caused by the flow path up to the column at the current flow rate. In some systems, the length and size of the flow path between the system pressure sensor 200 and the column 240, may be standardized, so that the predefined parameters may be used for the calculations. In other systems, (which is the most common situation), the flow path between components in the chromatography system is user defined, whereby a user of the system has to enter said parameters using by a user interface. According to one embodiment, the major part of the flow path between the system pressure sensor 200 and the column 240 may be comprised of capillary tubing of the same diameter, then the flow path characteristics may be estimated as the total length of the tubing, thus excluding contributions from other components, like valves or the like from the calculations. In other embodiments, the contribution from valves or the like in the flow path are taken into consideration and may be system defined, whereas, tubing or the like is user defined. It should be noted that, in case the flow path comprises sections of different size (e.g. tubing of different inner diameter), the pressure drop over each section has to be calculated individually and eventually added together to provide the total pressure drop.

When the pressure drop in the flow path up to the column 240 is estimated by the above calculations, the virtual Pre-column pressure is calculated by subtracting the pressure drop from the system pressure registered by system pressure sensor 200

Example: If System pressure is 5 bar and the calculated pressure drop over the flow path is 2 bar then the calculated virtual pre-column pressure is estimated to 3 bar.

All pressure contributions after the virtual pressure sensor will automatically be compensated for since these will directly affect the measured system pressure. So, e.g. if a flow restrictor is added or removed, the measured System pressure will change as well as the calculated Pre-column pressure. Changes in the flow path between the System pressure sensor and the column must be taken care of in the estimation.

According to one embodiment, in case the viscosity is not known, the controller may assume that water is used whereby the viscosity can be estimated for different temperatures using a known expression like:

$$V\ [cP]=A\times 10B/(T-C) \text{ where } T=\text{temperature [K]};$$
$$A=0.02414;\ B=247.8\ K;\ C=140\ K.$$

In the real situation there may be some factors that may affect the accuracy of the virtual pressure estimation. If the viscosity of the liquid is unknown and it is assumed to be water, but it has a higher viscosity, then the estimated value for flow path ΔP becomes too low. Then the calculated value for the virtual pressure signal becomes higher than the actual value whereby a pressure alarm will trigger before the actual pressure becomes too high for the column. This is also the case if other components in the flow path (mixer, valves etc) generate some back pressure. Consequently, for liquids with viscosity lower than water, the estimation will give a virtual pre-column pressure that is lower than the actual pressure. However, such liquids are mostly used for high pressure columns where the high accuracy of the pressure signal is not required since most such column withstand higher pressures than they are normally used with.

According to one embodiment, the system is arranged to estimate the delta-column pressure by using the same principles for the flow path after the column a virtual post-column pressure may be estimated and used to calculate a virtual delta-column pressure.

As mentioned, the virtual pre-column pressure and the delta-column pressure may be used to control the operation of the chromatography system, e.g. by monitoring said pressures with respect to predefined or user-defined pressure limits, or by running the chromatographic system at a predefined column pressure or the like.

There is further provided a method for controlling a chromatography system according to above comprising the steps:

registering the system pressure at a flow path position close to the system pump, controlling the operation of the system pump in response to the registered system pressure, estimating a pre-column pressure based on the registered system pressure, the characteristics of the flow path, and the viscosity and flow-rate of the liquid in the system, and controlling the operation of the system pump in response to the estimated pre-column pressure with respect to a pre-defined column pressure limit.

The invention claimed is:

1. A method for controlling a liquid chromatography system while pumping a fluid having a viscosity through the system at a given flow rate,
   the system comprising
      a computer operated system controller,
      a system pressure sensor,
      a system pump,
      a mixer for mixing fluids from the system pump,
      an injection valve downstream of the mixer,
      a column, and
      a fluid flow path having a length and a diameter, and in fluid communication with and between the system pump and the column, having a first position close to the system pump and upstream of the mixer and a second position that is directly upstream of said column and downstream of the first position,
   wherein
      the system pump is upstream of the mixer and the column, and
      the pump and the system pressure sensor are controlled by the computer operated system controller,
   the method comprising:
      using the system pressure sensor at the first position of the fluid flow path to register a system pressure using the controller,
      controlling the operation of the system pump in response to the registered system pressure using the controller,
      estimating a pre-column pressure at the second position based on the registered system pressure, the characteristics of the fluid flow path, and the viscosity and flow-rate of the liquid in the system using the controller, and
      controlling the system pump in response to the estimated pre-column pressure using the controller.

2. The method of claim 1, wherein the pre-column pressure is estimated based on Bernoulli's formula that has been programmed into the controller:

$$\text{pre-}P\ [MPa]=0.000000000679*L*Q*V/D^4$$

wherein
   L=length of the fluid flow path [mm] between the system pressure sensor and the column
   D=diameter of the fluid flow path [mm] between the system pressure sensor and the column
   Q=flow rate [ml/min]
   V=viscosity [cP].

3. The method of claim 1, wherein controlling the system pump in response to the estimated pre-column pressure involves restricting the pre-column pressure below a pre-defined value that has been programmed into the controller.

4. The method of claim 3, wherein the predefined value is a pressure limit for the column.

5. The method of claim 4, wherein the pressure limit for the column is accessed from a columns property table stored in the controller.

6. A method for controlling a liquid chromatography system while pumping a fluid having a viscosity through the system at a given flow rate, the system comprising
- a computer operated system controller,
- a system pressure sensor,
- a system pump,
- a mixer for mixing fluids from the system pump,
- an injection valve downstream of the mixer,
- a column, and
- a fluid flow path having a length and a diameter, and in fluid communication with and between the system pump and the column, having a first position close to the system pump and upstream of the mixer, a second position that is directly upstream of said column and downstream of the first position, and a third position that is after said column, wherein
- the system pump is upstream of the mixer and the column, and
- the pump and the system pressure sensor are controlled by the computer operated system controller, the method comprising:
- using the system pressure sensor at the first position of the fluid flow path to register a system pressure using the controller,
- controlling the operation of the system pump in response to the registered system pressure using the controller,
- estimating a pre-column pressure at the second position and a post-column pressure at the third position based on the registered system pressure, the characteristics of the fluid flow path, and the viscosity and flow-rate of the liquid in the system using the controller,
- obtaining a virtual delta-column pressure based on the pre-column pressure and the post-column pressure, and
- controlling the system pump in response to the virtual delta-column pressure using the controller.

7. The method of claim 6, wherein the pre-column and the post-column pressures are estimated based on Bernoulli's formula that has been programmed into the controller:

$$\text{pre-}P \text{ [MPa]} = 0.000000000679 * L * Q * V / D^4$$

wherein
L=length of the fluid flow path [mm] between the system pressure sensor and the column
D=diameter of the fluid flow path [mm] between the system pressure sensor and the column
Q=flow rate [ml/min]
V=viscosity [cP].

8. The method of claim 6, wherein controlling the system pump in response to the virtual delta-column pressure involves restricting the delta-column pressure below a predefined value that has been programmed into the controller.

9. The method of claim 8, wherein the predefined value is a pressure limit for the column.

10. The method of claim 4, wherein the pressure limit for the column is accessed from a columns property table stored in the controller.

* * * * *